US011220656B2

(12) United States Patent
Goedegebuur et al.

(10) Patent No.: US 11,220,656 B2
(45) Date of Patent: Jan. 11, 2022

(54) AUTOMATIC DISHWASHING DETERGENT COMPOSITION

(71) Applicant: The Procter & Gamble Company, Cincinnati, OH (US)

(72) Inventors: Frits Goedegebuur, Vlaardingen (NL); David Aaron Estell, San Mateo, CA (US); Lilia Maria Babe, Emerald Hills, CA (US); Thijs Kaper, Half Moon Bay, CA (US); Viktor Alekseyev, Palo Alto, CA (US); Sina Pricelius, Leiden (NL); Hatice Billur Engin, Mountain View, CA (US); Harm Jan Mulder, Voorhout (NL); Sander Van Stigt-Thans, Nieuwerkerk aan den IJssel (NL); Eva Maria Perez-Prat Vinuesa, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/439,731

(22) Filed: Jun. 13, 2019

(65) Prior Publication Data
US 2020/0010782 A1    Jan. 9, 2020

Related U.S. Application Data

(60) Provisional application No. 62/686,833, filed on Jun. 19, 2018, provisional application No. 62/852,321, filed on May 24, 2019.

(51) Int. Cl.
| | | |
|---|---|---|
| *C11D 3/386* | (2006.01) | |
| *A47L 15/44* | (2006.01) | |
| *C11D 1/00* | (2006.01) | |
| *C11D 3/10* | (2006.01) | |
| *C11D 3/20* | (2006.01) | |
| *C11D 3/33* | (2006.01) | |
| *C11D 3/395* | (2006.01) | |
| *C11D 11/00* | (2006.01) | |

(52) U.S. Cl.
CPC ...... *C11D 3/38618* (2013.01); *A47L 15/4418* (2013.01); *C11D 1/008* (2013.01); *C11D 3/10* (2013.01); *C11D 3/2086* (2013.01); *C11D 3/33* (2013.01); *C11D 3/3951* (2013.01); *C11D 11/0023* (2013.01)

(58) Field of Classification Search
None
See application file for complete search history.

(56) References Cited

U.S. PATENT DOCUMENTS

| | | |
|---|---|---|
| 7,449,187 B2 | 11/2008 | Weber |
| 2009/0275493 A1 | 11/2009 | Siegert |
| 2016/0319266 A1 | 11/2016 | Kolkman |
| 2018/0002642 A1 | 1/2018 | Kolkman |
| 2018/0023069 A1 | 1/2018 | Hellmuth |
| 2019/0144792 A1 | 5/2019 | Herbst |
| 2019/0194636 A1 | 6/2019 | Babe |
| 2020/0024552 A1 | 1/2020 | Goedegebuur |

FOREIGN PATENT DOCUMENTS

| | | |
|---|---|---|
| WO | WO2009037258 A1 | 3/2009 |
| WO | 2015044206 A1 | 4/2015 |
| WO | WO2016205755 A1 | 12/2016 |
| WO | WO2018118917 A1 | 6/2018 |
| WO | WO2018118950 A1 | 6/2018 |
| WO | WO2019108599 A1 | 6/2019 |

OTHER PUBLICATIONS

All Office Actions; U.S. Appl. No. 16/439,728.
International Search Report and Written Opinion; Application Ser. No. PCT/US2019/036889; dated Oct. 30, 2019, 20 pages.
Invitation to Pay Additional Fees; International Application No. PCT/US2019/036888; dated Aug. 30, 2019; 17 pages.
Invitation To Pay Additional Fees; International Application No. PCT/US2019/036889; dated Aug. 30, 2019; 15 pages.
U.S. Appl. No. 16/439,728, filed Jun. 13, 2019, Goedegebuur, et al.

*Primary Examiner* — Kagnew H Gebreyesus
(74) *Attorney, Agent, or Firm* — George H. Leal

(57) ABSTRACT

An automatic dishwashing cleaning composition having a new protease.

13 Claims, No Drawings

Specification includes a Sequence Listing.

SEQUENCE LISTING

```
<160> NUMBER OF SEQ ID NOS: 2

<210> SEQ ID NO 1
<211> LENGTH: 269
<212> TYPE: PRT
<213> ORGANISM: Bacillus gibsonii

<400> SEQUENCE: 1

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Thr Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Ala Glu Gly
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255
```

```
Phe Gly Ser Gly Leu Val Asn Ala Glu Ala Ala Thr Arg
            260                 265
```

```
<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
 1               5                  10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365
```

```
Gly Asp Tyr Tyr Gly Ile Pro Thr His Gly Val Pro Ala Met Lys Ser
    370             375             380

Lys Ile Asp Pro Ile Leu Glu Ala Arg Gln Lys Tyr Ala Tyr Gly Arg
385             390             395             400

Gln Asn Asp Tyr Leu Asp His His Asn Ile Ile Gly Trp Thr Arg Glu
            405             410             415

Gly Asn Thr Ala His Pro Asn Ser Gly Leu Ala Thr Ile Met Ser Asp
            420             425             430

Gly Ala Gly Gly Asn Lys Trp Met Phe Val Gly Arg Asn Lys Ala Gly
        435             440             445

Gln Val Trp Thr Asp Ile Thr Gly Asn Arg Ala Gly Thr Val Thr Ile
    450             455             460

Asn Ala Asp Gly Trp Gly Asn Phe Ser Val Asn Gly Gly Ser Val Ser
465             470             475             480

Ile Trp Val Asn Lys
            485
```

AUTOMATIC DISHWASHING DETERGENT COMPOSITION

FIELD OF THE INVENTION

The present invention is in the field of detergents. In particular, it relates to an automatic dishwashing detergent comprising a specific protease. The composition provides improved removal of proteinaceous soils versus compositions comprising conventional proteases.

BACKGROUND OF INVENTION

There is a permanent desire to improve the performance of automatic dishwashing compositions and their environmental profile.

Due to environmental concerns phosphate is increasingly being replaced by biodegradable complexing agents. These complexing agents can have a strong binding capacity for metals and/or are used in high levels and can negatively affect the stability of enzymes, in particular complexing agents can negatively affect proteases by extracting the structural calcium metal ions of the protease. The proteases can be affected in product and/or in-use. While compositions having a high level of bleach can provide good cleaning the bleach can also impair on the performance of enzymes, specifically proteases. This effect can be exacerbated by high level of complexing agents, high temperature and long cycles.

Automatic dishwashing compositions can be designed to have optimum performance under certain in-use conditions, for example a composition can be designed to have optimum performance in a soft water cycle, however a composition that has optimum performance in soft water might not have optimum performance in a hard water cycle and vice versa.

The object of the present invention is to provide a dishwashing composition that provides better removal of proteinaceious soils. Preferably, the removal should be good when the composition is used in soft water and preferably under different water hardness conditions It is also desirable that the composition has improved stability and provides improved performance even under stressed conditions such as heavily soiled load washed in hot, long cycles.

SUMMARY OF THE INVENTION

According to the first aspect of the present invention, there is provided an automatic dishwashing detergent composition comprising a specific protease. The composition is preferably a phosphate-free automatic dishwashing cleaning composition. More preferably, the composition comprises a complexing agent system, and more preferably the composition comprises a complexing agent system and high level of a bleaching system. The composition presents improved stability and/or performance on egg and/or creme brulee removal. The composition of the invention can be suitable for soft water and/or high temperatures and/or long cycles are used in automatic dishwashing.

According to the second aspect of the invention there is provided a method of automatic dishwashing using the composition of the invention. The use of a composition according to the invention to provide creme brulee removal in automatic dishwashing.

The elements of the composition of the invention described in connexion with the first aspect of the invention apply mutatis mutandis to the other aspects of the invention.

DETAILED DESCRIPTION OF THE INVENTION

The present invention encompasses an automatic dishwashing cleaning composition comprising a specific protease. The composition is preferably phosphate-free and preferably comprises a complexing agent system. The composition delivers improved cleaning versus cleaning compositions comprising conventional proteases under a plurality of conditions. The composition provides good proteinaceous cleaning, in particular on egg and creme brulee soils. The invention also encompasses methods of automatic dishwashing. The composition of the invention provides good cleaning in hot, long cycles and when using soft water.

By "soft" water is herein meant water having a hardness of less than about 2 gpg (34.3 ppm). Grain per gallon (gpg) is a unit of water hardness defined as 1 grain (64 8 milligrams) of calcium carbonate dissolved in 1 US gallon of water (3.785412 L). It translates into 17.1 parts per million (ppm).

By "hot" cycle is herein understood a dishwashing program in which the main cycle is performed at a temperature above 50° C., preferably above 55° C.

By "long" cycle is herein understood a dishwashing program in which the main cycle has a duration of at least 25, preferably at least 30 and more preferably at least 35 minutes.

The composition of the invention comprises a variant protease, the variant proteases have a defined percentage of identity with respect to a reference protease (protease of SEQ ID NO: 1).

The protease of the composition of the invention is herein sometimes referred to as "the protease of the invention". The protease having SEQ ID NO:1 is herein sometimes referred to as "the reference protease".

The relatedness between two amino acid sequences or between two nucleotide sequences is described by the parameter "sequence identity".

The term "variant" means a protease comprising a mutation, i.e., a substitution, insertion, and/or deletion, at one or more (e.g., several) positions relative to the reference protease. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 90%, preferably at least 92%, more preferably a least 95% and especially 99% identity with the reference protease.

The term "wild-type" protease means a protease expressed by a naturally occurring microorganism, such as a bacterium, yeast, or filamentous fungus found in nature. In some embodiments, the reference polypeptide comprises a *B. gibsonii*-clade subtilisin.

In some embodiments, the reference polypeptide, as provided herein, comprises a *B. gibsonii*-clade subtilisin having the amino acid sequence set forth in SEQ ID NO:1.

Enzyme Related Terminology

Nomenclature for Amino Acid Modifications

In describing enzyme variants herein, the following nomenclature is used for ease of reference: Original amino acid(s): position (s): substituted amino acid(s).

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific enzyme contains a "deletion" in comparison with other enzyme and an insertion is made in such a position this is indicated as *36D for insertion of an aspartic acid in position 36. Multiple mutations are separated by pluses, i.e.: S99G+V102N, representing mutations in positions 99 and 102 substituting serine and valine for glycine and asparagine, respectively. Where the amino acid in a position (e.g. 102) may be substituted by another amino acid selected from a group of amino acids, e.g. the group consisting of N and I, this will be indicated by V102N, I.

In all cases, the accepted IUPAC single letter or triple letter amino acid abbreviation is employed.

Protease Amino Acid Numbering

The numbering used in this patent is versus SEQ ID NO:1.

Amino Acid Identity

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of an enzyme used herein ("invention sequence") and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity. An exact match occurs when the "invention sequence" and the "foreign sequence" have identical amino acid residues in the same positions of the overlap. The length of a sequence is the number of amino acid residues in the sequence.

The term "succinate based compound" and "succinic acid based compound" are used interchangeably herein.

As used herein, articles such as "a" and "an" when used in a claim, are understood to mean one or more of what is claimed or described.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

The Protease of the Invention

The variant of the present invention has at least 90%, more preferably at least 92% more preferably at least 95% and specially at least 99% identity with the protease of SEQ ID NO: 1 and comprises one or more amino acid substitutions at one or more positions selected from:

(i) 1C/D/E/M/N, 21L, 37A, 54A, 73V, 76D/H/N/T, 83G, 84D/E/F, 85I/M, 86I/S/T/V, 87T, 88M/V, 89F/W, 91I, 95A/N/S, 96M/Q, 97E, 98M, 99A/F/H/I/K/L/Q/T/W/Y, 102L, 104E, 105L, 106I/V, 108A, 109I, 112C, 114M/N, 115A/E/H/Q, 116A/E/G/H/Q, 118A/D/N, 122C, 124E/Q, 126I/Q/V, 128H/I/L/M/N/Q/S/T/V/Y, 129D/H, 130N, 131D/E/N/P/Q, 135A/D/H/K/L/M/N/Q/T/V/W/Y, 138D/E, 139E/L, 141A/E/F/H/Y, 142A/D/E, 143E/H/K/M/S/V, 156E, and 157C/D/E wherein the amino acid positions of the variant are numbered by correspondence with the amino acid sequence of SEQ ID NO: 1.

Preferably, the variant comprises at least two, more preferably at least three, more preferably at least four amino acid substitutions (using the SEQ ID NO:1 numbering)

The compositions are very good for the removal of egg, creme brulee and/or present good stability. It is particularly good for the removal of creme brulee.

A preferred composition, in terms of creme brulee removal, comprises a variant having at least 90%, more preferably at least 92%, more preferably at least 95% and specially at least 99% identity with the protease of SEQ ID NO: 1 and comprises one or more amino acid substitutions at one or more positions selected from: 1D; 21L; 37A; 73V; 76D; 84D/E; 85M; 86I/V; 87T; 96M; 97E; 99A/F/H/I/L/Q/T/W/Y; 104E; 106I/V; 115A/E; 116E; 122C; 126I/Q/V; 128S/T/V; 129D; 130N; 131D/E; 135A/D/H/L/M/N/Q/T/V/W/Y; 138D; 139E/L; 141E/Y; 142D/E; 143E/H/M/V; 156E; and 157C/D/E.

The variant has at least 90% identity with the amino acid sequence of SEQ ID NO:1 and preferably comprises at least three substitutions.

Especially preferred variants for use in the composition of the invention are selected from the group consisting of variants having at least 90%, more preferably at least 92%, more preferably at least 95% and specially at least 99% identity with the amino acid sequence SEQ ID:1.

In one embodiment the composition comprises a protease wherein the protease is a variant having at least 90% identity with the amino acid sequence of SEQ ID NO:1 and the variant comprises one or more amino acid substitutions at one or more positions corresponding to SEQ ID NO:1 positions selected from: 1C/D/E/M/N, 21L, 37A, 54A, 73V, 76D/H/N/T, 83G, 84D/E/F, 85I/M, 86I/S/T/V, 87T, 88M/V, 89F/W, 91I, 95A/N/S, 96M/Q, 97E, 98M, 99A/F/H/I/K/L/Q/T/W/Y, 102L, 104E, 105L, 106I/V, 108A, 109I, 112C, 114M/N, 115A/E/H/Q, 116A/E/G/H/Q, 118A/D/N, 122C, 124E/Q, 126I/Q/V, 128H/I/L/M/N/Q/S/T/V/Y, 129D/H, 130N, 131D/E/N/P/Q, 135A/D/H/K/L/M/N/Q/T/V/W/Y, 138D/E, 139E/L, 141A/E/F/H/Y, 142A/D/E, 143E/H/K/M/S/V, 156E, and 157C/D/E; wherein the amino acid positions of the variant are numbered by correspondence with the amino acid sequence of SEQ ID NO:1.

In some embodiments, the variant protease also comprises at least one, two, three, or more additional substitutions selected from Q012E, Q037E, NO60D, N097D, Q107E, N115D, N154D, N167D, Q176E, Q185E, Q200E, N205D, Q230E, N236D, N242D, N250D, N253D, Q256E, N253D-Q256E, G025R-M117I-H118N, A149S, $R_{044}$P-D175N-Y208N-Q230H, L041F-G078D-P084A, S101G-T174A, I021V-N177I, I021V-S142G-T188A, I021V-M122L-A222S, Q012L-I021V-M122L-A222S, I1021V-M122L-N253D, I021V-N177V-V228I, I021V-S039T-M122L-N177E, I021V-V079L-D087E-A209N-A222S, I021V-M122L-A222S-T247N, I021V-M122L, S039E-N074D-D087E, N253P, 5039E-N074D-D087E-N253D, I021V-S039E-N074D-D087E-N253D, 5039E-N074D-D087E-M122L-N253D, I021V-S039E-N074D-D087E-M122L-N253D, I021V, M122L, M211S, P212N, Q012L, N177V, A222S, V228I, T274N, $R_{099}$E, N097D-$R_{099}$E, S097D, S099E, I043V, M122L-N145S-T156A, M211N-P212D, M211L-P212D, G160S, D127P-M211L-P212D, P212H, Q012L-M122L-A222S, D127P, N145S, T156A, M211N, and P212D.

A further embodiment is directed to a method of automatic dishwashing, in particular cleaning a crème brûlée stain comprising contacting a surface or an item in need of cleaning with a composition comprising a protease wherein the protease is a variant having at least 90% identity with the amino acid sequence of SEQ ID NO:1 and the variant comprises one or more substitutions at one or more positions corresponding to SEQ ID NO:1 positions selected from: 1C/D/E/N, 21L, 37A, 73V, 76D/H/N, 84D/E, 85M, 95A, 96M/Q, 97E, 99A/H/Q/T, 104E, 115E, 116E/G, 129D, 131D/E, 135H/K/L/M/Q/T/V/W/Y, 138D, 139E/L, 141E/H/Y, 142D/E, 143E/H/K/M/S/V, 156E, and 157D/E and combinations; wherein the amino acid positions of the variant are numbered by correspondence with the amino acid sequence of SEQ ID NO:1.

The protease of the invention performs very well in phosphate-free compositions even when the compositions are used in soft water.

Preferred levels of protease in the composition of the invention include from about 0.04 to about 5 mg, more preferably from about 0.05 to about 2 mg of active protease per gram of the composition.

Automatic Dishwashing Cleaning Composition

The automatic dishwashing cleaning composition can be in any physical form. It can be a loose powder, a gel or presented in unit dose form. Preferably it is in unit dose form, unit dose forms include pressed tablets and water-soluble packs. The automatic dishwashing cleaning composition of the invention is preferably presented in unit-dose form and it can be in any physical form including solid, liquid and gel form. The composition of the invention is very well suited to be presented in the form of a multi-compartment pack, more in particular a multi-compartment pack comprising compartments with compositions in different physical forms, for example a compartment comprising a composition in solid form and another compartment comprising a composition in liquid form. The composition is preferably enveloped by a water-soluble film such as polyvinyl alcohol. Especially preferred are compositions in unit dose form wrapped in a polyvinyl alcohol film having a thickness of less than 100 µm, preferably from 20 to 90 µm. The detergent composition of the invention weighs from about 8 to about 25 grams, preferably from about 10 to about 20 grams. This weight range fits comfortably in a dishwasher dispenser. Even though this range amounts to a low amount of detergent, the detergent has been formulated in a way that provides all the benefits mentioned herein above.

The composition is preferably phosphate free. By "phosphate-free" is herein understood that the composition comprises less than 1%, preferably less than 0.1% by weight of the composition of phosphate.

The composition of the invention is preferably phosphate-free and comprises a complexing agent system.

Complexing Agent System

For the purpose of this invention a "complexing agent" is a compound capable of binding polyvalent ions such as calcium, magnesium, lead, copper, zinc, cadmium, mercury, manganese, iron, aluminium and other cationic polyvalent ions to form a water-soluble complex. The complexing agent has a logarithmic stability constant ([log K]) for Ca2+ of at least 3. The stability constant, log K, is measured in a solution of ionic strength of 0.1, at a temperature of 25° C. The composition of the invention comprises from 10% to 50% by weight of the composition of a complexing agent system. Preferably, the composition comprises a complexing agent selected from the group consisting of citric acid, methyl glycine diacetic acid (MGDA), glutamic-N,N-diacetic acid (GLDA), iminodisuccinic acid (IDS), carboxy methyl inulin, L-Aspartic acid N, N-diacetic acid tetrasodium salt (ASDA) and mixtures thereof. For the purpose of this invention, the term "acid", when referring to complexing agents, includes the acid and salts thereof.

In a preferred embodiment, the composition comprises from 15% to 40% by weight of the invention of MGDA, more preferably the tri-sodium salt of MGDA. Compositions comprising this high level of MGDA perform well in the presence of hard water and also in long and/or hot cycles.

In a preferred embodiment, the composition comprises from 15% to 28% by weight of the invention of citric acid, more preferably sodium citrate. Compositions comprising citric acid perform well in the presence of soft water.

In a preferred embodiment, the complexing agent system comprises citric acid and MGDA, preferably in a weight ratio of from about 0.5:1 to about 2:1, more preferably from about 0.5:1 to about 2.5:1.

Dispersant Polymer

A dispersant polymer can be used in any suitable amount from about 0.1 to about 20%, preferably from 0.2 to about 15%, more preferably from 0.3 to % by weight of the composition.

The dispersant polymer is capable to suspend calcium or calcium carbonate in an automatic dishwashing process.

The dispersant polymer has a calcium binding capacity within the range between 30 to 250 mg of Ca/g of dispersant polymer, preferably between 35 to 200 mg of Ca/g of dispersant polymer, more preferably 40 to 150 mg of Ca/g of dispersant polymer at 25° C. In order to determine if a polymer is a dispersant polymer within the meaning of the invention, the following calcium binding-capacity determination is conducted in accordance with the following instructions:

Calcium Binding Capacity Test Method

The calcium binding capacity referred to herein is determined via titration using a pH/ion meter, such as the Meettler Toledo SevenMulti™ bench top meter and a PerfectION™ comb Ca combination electrode. To measure the binding capacity a heating and stirring device suitable for beakers or tergotometer pots is set to 25° C., and the ion electrode with meter are calibrated according to the manufacturer's instructions. The standard concentrations for the electrode calibration should bracket the test concentration and should be measured at 25° C. A stock solution of 1000 mg/g of Ca is prepared by adding 3.67 g of $CaCl_2$-$2H_2O$ into 1 L of deionised water, then dilutions are carried out to prepare three working solutions of 100 mL each, respectively comprising 100 mg/g, 10 mg/g, and 1 mg/g concentrations of Calcium. The 100 mg Ca/g working solution is used as the initial concentration during the titration, which is conducted at 25° C. The ionic strength of each working solution is adjusted by adding 2.5 g/L of NaCl to each. The 100 mL of 100 mg Ca/g working solution is heated and stirred until it reaches 25° C. The initial reading of Calcium ion concentration is conducted at when the solution reaches 25° C. using the ion electrode. Then the test polymer is added incrementally to the calcium working solution (at 0.01 g/L intervals) and measured after 5 minutes of agitation following each incremental addition. The titration is stopped when the solution reaches 1 mg/g of Calcium. The titration procedure is repeated using the remaining two calcium concentration working solutions. The binding capacity of the test polymer is calculated as the linear slope of the calcium concentrations measured against the grams/L of test polymer that was added.

The dispersant polymer preferably bears a negative net charge when dissolved in an aqueous solution with a pH greater than 6.

The dispersant polymer can bear also sulfonated carboxylic esters or amides, in order to increase the negative charge at lower pH and improve their dispersing properties in hard water. The preferred dispersant polymers are sulfonated/carboxylated polymers, i.e., polymer comprising both sulfonated and carboxylated monomers.

Preferably, the dispersant polymers are sulfonated derivatives of polycarboxylic acids and may comprise two, three, four or more different monomer units. The preferred copolymers contain:

At least one structural unit derived from a carboxylic acid monomer having the general formula (III):

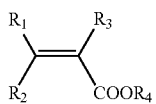

(III)

wherein $R_1$ to $R_3$ are independently selected from hydrogen, methyl, linear or branched saturated alkyl groups having from 2 to 12 carbon atoms, linear or branched mono or polyunsaturated alkenyl groups having from 2 to 12 carbon atoms, alkyl or alkenyl groups as aforementioned substituted with —NH2 or —OH, or —COOH, or $COOR_4$, where $R_4$ is selected from hydrogen, alkali metal, or a linear or branched, saturated or unsaturated alkyl or alkenyl group with 2 to 12 carbons;

Preferred carboxylic acid monomers include one or more of the following: acrylic acid, maleic acid, maleic anhydride, itaconic acid, citraconic acid, 2-phenylacrylic acid, cinnamic acid, crotonic acid, fumaric acid, methacrylic acid, 2-ethylacrylic acid, methylenemalonic acid, or sorbic acid. Acrylic and methacrylic acids being more preferred.

Optionally, one or more structural units derived from at least one nonionic monomer having the general formula (IV):

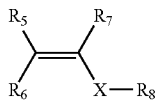

(IV)

Wherein $R_5$ to $R_7$ are independently selected from hydrogen, methyl, phenyl or hydroxyalkyl groups containing 1 to 6 carbon atoms, and can be part of a cyclic structure, X is an optionally present spacer group which is selected from —CH$_2$—, —COO—, —CONH— or —CONR$_8$—, and $R_8$ is selected from linear or branched, saturated alkyl radicals having 1 to 22 carbon atoms or unsaturated, preferably aromatic, radicals having from 6 to 22 carbon atoms.

Preferred non-ionic monomers include one or more of the following: butene, isobutene, pentene, 2-methylpent-1-ene, 3-methylpent-1-ene, 2,4,4-trimethylpent-1-ene, 2,4,4-trimethylpent-2-ene, cyclopentene, methylcyclopentene, 2-methyl-3-methyl-cyclopentene, hexene, 2,3-dimethylhex-1-ene, 2,4-dimethylhex-1-ene, 2,5-dimethylhex-1-ene, 3,5-dimethylhex-1-ene, 4,4-dimethylhex-1-ene, cyclohexene, methylcyclohexene, cycloheptene, alpha olefins having 10 or more carbon atoms such as, dec-1-ene, dodec-1-ene, hexadec-1-ene, octadec-1-ene and docos-1-ene, preferred aromatic monomers are styrene, alpha methylstyrene, 3-methylstyrene, 4-dodecylstyrene, 2-ethyl-4-bezylstyrene, 4-cyclohexylstyrene, 4-propylstyrol, 1-vinylnaphtalene, 2-vinylnaphtalene; preferred carboxylic ester monomers are methyl (meth)acrylate, ethyl (meth)acrylate, propyl (meth)acrylate, t-butyl (meth)acrylate, pentyl (meth)acrylate, hexyl (meth)acrylate, 2-ethylhexyl (meth)acrylate, octyl (meth)acrylate, lauryl (meth)acrylate, stearyl (meth)acrylate and behenyl (meth)acrylate; preferred amides are N-methyl acrylamide, N-ethyl acrylamide, N-t-butyl acrylamide, N-2-ethylhexyl acrylamide, N-octyl acrylamide, N-lauryl acrylamide, N-stearyl acrylamide, N-behenyl acrylamide.

and at least one structural unit derived from at least one sulfonic acid monomer having the general formula (V) and (VI):

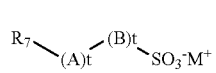

(V)

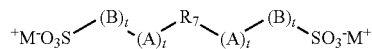

(VI)

wherein $R_7$ is a group comprising at least one sp2 bond, A O, N, P, S, an amido or ester linkage, B is a mono- or polycyclic aromatic group or an aliphatic group, each t is independently 0 or 1, and M+ is a cation. In one aspect, $R_7$ is a C2 to C6 alkene. In another aspect, $R_7$ is ethene, butene or propene.

Preferred sulfonated monomers include one or more of the following: 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propen-1-sulfonic acid, styrenesulfonic acid, vinylsulfonic acid, 3-sulfopropyl, 3-sulfopropylmethacrylate, sulfomethacrylamide, sulfomethylmethacrylamide and mixtures of said acids or their water-soluble salts.

Preferably, the polymer comprises the following levels of monomers: from about 40 to about 90%, preferably from about 60 to about 90% by weight of the polymer of one or more carboxylic acid monomer; from about 5 to about 50%, preferably from about 10 to about 40% by weight of the polymer of one or more sulfonic acid monomer; and optionally from about 1% to about 30%, preferably from about 2 to about 20% by weight of the polymer of one or more non-ionic monomer. An especially preferred polymer comprises about 70% to about 80% by weight of the polymer of at least one carboxylic acid monomer and from about 20% to about 30% by weight of the polymer of at least one sulfonic acid monomer.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

The carboxylic acid is preferably (meth)acrylic acid. The sulfonic acid monomer is preferably 2-acrylamido-2-propanesulfonic acid (AMPS).

Preferred commercially available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas.

Suitable dispersant polymers include anionic carboxylic polymer of low molecular weight. They can be homopolymers or copolymers with a weight average molecular weight of less than or equal to about 200,000 g/mol, or less than or equal to about 75,000 g/mol, or less than or equal to about 50,000 g/mol, or from about 3,000 to about 50,000 g/mol, preferably from about 5,000 to about 45,000 g/mol. The dispersant polymer may be a low molecular weight homopolymer of polyacrylate, with an average molecular weight of from 1,000 to 20,000, particularly from 2,000 to 10,000, and particularly preferably from 3,000 to 5,000.

The dispersant polymer may be a copolymer of acrylic with methacrylic acid, acrylic and/or methacrylic with maleic acid, and acrylic and/or methacrylic with fumaric acid, with a molecular weight of less than 70,000. Their molecular weight ranges from 2,000 to 80,000 and more preferably from 20,000 to 50,000 and in particular 30,000 to 40,000 g/mol. and a ratio of (meth)acrylate to maleate or fumarate segments of from 30:1 to 1:2.

The dispersant polymer may be a copolymer of acrylamide and acrylate having a molecular weight of from 3,000 to 100,000, alternatively from 4,000 to 20,000, and an acrylamide content of less than 50%, alternatively less than 20%, by weight of the dispersant polymer can also be used. Alternatively, such dispersant polymer may have a molecular weight of from 4,000 to 20,000 and an acrylamide content of from 0% to 15%, by weight of the polymer.

Dispersant polymers suitable herein also include itaconic acid homopolymers and copolymers.

Alternatively, the dispersant polymer can be selected from the group consisting of alkoxylated polyalkyleneimines, alkoxylated polycarboxylates, polyethylene glycols, styrene co-polymers, cellulose sulfate esters, carboxylated polysaccharides, amphiphilic graft copolymers and mixtures thereof.

Bleaching System

The composition of the invention comprises a bleaching system comprising a high level of bleach, preferably percarbonate in combination with a bleach activator or a bleach catalyst or both. Preferably the bleach activator is TAED and the bleach catalyst is a manganese bleach catalyst.

Bleach

The composition of the invention preferably comprises from about 10 to about 20%, more preferably from about 12 to about 18% of bleach, preferably percarbonate, by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein. Typical organic bleaches are organic peroxyacids, especially dodecanediperoxoic acid, tetradecanediperoxoic acid, and hexadecanediperoxoic acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane -1,4-dioic acid, N,N-terephthaloyldi (6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 12 carbon atoms, in particular from 2 to 10 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro -1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), decanoyloxybenzoic acid (DOBA), carboxylic anhydrides, in particular phthalic anhydride, acylated polyhydric alcohols, in particular triacetin, ethylene glycol diacetate and 2,5-diacetoxy -2,5-dihydrofuran and also triethylacetyl citrate (TEAC). If present the composition of the invention comprises from 0.01 to 5, preferably from 0.2 to 2% by weight of the composition of bleach activator, preferably TAED.

Bleach Catalyst

The composition herein preferably contains a bleach catalyst, preferably a metal containing bleach catalyst. More preferably the metal containing bleach catalyst is a transition metal containing bleach catalyst, especially a manganese or cobalt-containing bleach catalyst. Bleach catalysts preferred for use herein include manganese triazacyclononane and related complexes; Co, Cu, Mn and Fe bispyridylamine and related complexes; and pentamine acetate cobalt(III) and related complexes. Especially preferred bleach catalyst for use herein are 1,4,7-trimethyl-1,4,7-triazacyclononane (Me-TACN) and 1,2,4,7-tetramethyl-1,4,7-triazacyclononane (Me/Me-TACN).

Preferably the composition of the invention comprises from 0.001 to 0.5, more preferably from 0.002 to 0.05%, more preferably from 0.005 to 0.075% of bleach catalyst by weight of the composition. Preferably the bleach catalyst is a manganese bleach catalyst.

Inorganic Builder

The composition of the invention preferably comprises an inorganic builder. Suitable inorganic builders are selected from the group consisting of carbonate, silicate and mixtures thereof. Especially preferred for use herein is sodium carbonate. Preferably the composition of the invention comprises from 5 to 60%, more preferably from 10 to 50% and especially from 15 to 45% of sodium carbonate by weight of the composition.

Surfactant

Surfactants suitable for use herein include non-ionic surfactants, preferably the compositions are free of any other surfactants. Traditionally, non-ionic surfactants have been used in automatic dishwashing for surface modification purposes in particular for sheeting to avoid filming and spotting and to improve shine. It has been found that non-ionic surfactants can also contribute to prevent redeposition of soils.

Preferably the composition of the invention comprises a non-ionic surfactant or a non-ionic surfactant system, more preferably the non-ionic surfactant or a non-ionic surfactant system has a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated nonionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

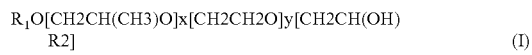

$$R_1O[CH_2CH(CH_3)O]_x[CH_2CH_2O]_y[CH_2CH(OH)R_2]\quad(I)$$

wherein R1 is a linear or branched, aliphatic hydrocarbon radical having from 4 to 18 carbon atoms; R2 is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH2CH(OH)R2]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

Enzymes

Other Proteases

The composition of the invention can comprise a protease in addition to the protease of the invention. A mixture of two or more proteases can contribute to an enhanced cleaning across a broader temperature, cycle duration, and/or substrate range, and provide superior shine benefits, especially when used in conjunction with an anti-redeposition agent and/or a sulfonated polymer.

Suitable proteases for use in combination with the variant proteases of the invention include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), especially those derived from Bacillus, such as Bacillus sp., B. lentus, B. alkalophilus, B. subtilis, B. amyloliquefaciens, B. pumilus , B. gibsonii, and B. akibaii described in WO2004067737, WO2015091989, WO2015091990, WO2015024739, WO2015143360, U.S. Pat. No. 6,312,936 B1, U.S. Pat. No. 5,679,630, U.S. Pat. No. 4,760,025, DE102006022216A1, DE102006022224A1, WO2015089447, WO2015089441, WO2016066756, WO2016066757, WO2016069557, WO2016069563, WO2016069569.

(b) trypsin-type or chymotrypsin-type proteases, such as trypsin (e.g., of porcine or bovine origin), including the Fusarium protease described in WO 89/06270 and the chymotrypsin proteases derived from Cellumonas described in WO 05/052161 and WO 05/052146.

(c) metalloproteases, especially those derived from Bacillus amyloliquefaciens decribed in WO07/044993A2; from Bacillus, Brevibacillus, Thermoactinomyces, Geobacillus, Paenibacillus, Lysinibacillus or Streptomyces spp. Described in WO2014194032, WO2014194054 and WO2014194117; from Kribella alluminosa described in WO2015193488; and from Streptomyces and Lysobacter described in WO2016075078.

(d) protease having at least 90% identity to the subtilase from Bacillus sp. TY145, NCIMB 40339, described in WO92/17577 (Novozymes A/S), including the variants of this *Bacillus* sp TY145 subtilase described in WO2015024739, and WO2016066757.

Especially preferred additional proteases for the detergent of the invention are polypeptides demonstrating at least 90%, preferably at least 95%, more preferably at least 98%, even more preferably at least 99% and especially 100% identity with the wild-type enzyme from *Bacillus lentus*, comprising mutations in one or more, preferably two or more and more preferably three or more of the following positions, using the BPN' numbering system and amino acid abbreviations as illustrated in WO00/37627, which is incorporated herein by reference:V68A, N76D, N87S, S99D, S99SD, S99A, S101G, S101M, S103A, V104N/I, G118V, G118R, S128L, P129Q, S130A, Y167A, $R_{170}S$, A194P, V205I, Q206L/D/E, Y209W and/or M222S.

Most preferably the additional protease is selected from the group of proteases comprising the below mutations (BPN' numbering system) versus either the PB92 wild-type (SEQ ID NO:2 in WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N
(vii) S99AD Suitable commercially available additional protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase®, Coronase®, Blaze®, Blaze Ultra® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase®, Ultimase® and Purafect OXP® by Dupont; those sold under the tradename Opticlean® and Optimase® by Solvay Enzymes; and those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D); and KAP (Bacillus alkalophilus subtilisin with mutations A230V+S256G+S259N) from Kao.

Especially preferred for use herein in combination with the variant protease of the invention are commercial proteases selected from the group consisting of Properase®, Blaze®, Ultimase®, Everlase®, Savinase®, Excellase®, Blaze Ultra®, BLAP and BLAP variants.

Preferred levels of protease in the product of the invention include from about 0.05 to about 10, more preferably from about 0.5 to about 7 and especially from about 1 to about 6 mg of active protease/g of composition.

Amylases

Preferably the composition of the invention may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCBI 12289, NCBI 12512, NCBI 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) variants described in WO 96/23873, WO00/60060, WO06/002643 and WO2017/192657, especially the variants with one or more substitutions in the following positions versus SEQ ID NO. 11:
26, 30, 33, 82, 37, 106, 118, 128, 133, 149, 150, 160, 178, 182, 186, 193, 202, 214, 231, 246, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.
(b) variants exhibiting at least 90% identity with SEQ ID No. 4 in WO06/002643, the wild-type enzyme from *Bacillus* SP722, especially variants with deletions in the 183 and 184 positions and variants described in WO 00/60060, WO2011/100410 and WO2013/003659which are incorporated herein by reference.
(c) variants exhibiting at least 95% identity with the wild-type enzyme from *Bacillus* sp.707 (SEQ ID NO:7 in U.S. Pat. No. 6,093, 562), especially those comprising one or more of the following mutations M202, M208, S255, $R_{172}$, and/or M261. Preferably said amylase comprises one or more of M202L, M202V, M2025, M202T, M202I, M202Q, M202W, S255N and/or $R_{172}Q$. Particularly preferred are those comprising the M202L or M202T mutations.
(d) variants described in WO 09/149130, preferably those exhibiting at least 90% identity with SEQ ID NO: 1 or SEQ ID NO:2 in WO 09/149130, the wild-type enzyme from Geobacillus Stearophermophilus or a truncated version thereof.
(e) variants exhibiting at least 89% identity with SEQ ID NO:1 in WO2016091688, especially those comprising deletions at positions H183+G184 and additionally one or more mutations at positions 405, 421, 422 and/or 428.
(f) variants exhibiting at least 60% amino acid sequence identity with the "PcuAmyl α-amylase" from *Paenibacillus curdlanolyticus* YK9 (SEQ ID NO:3 in WO2014099523).
(g) variants exhibiting at least 60% amino acid sequence identity with the "CspAmy2 amylase" from *Cytophaga* sp. (SEQ ID NO:1 in WO2014164777).
(h) variants exhibiting at least 85% identity with AmyE from *Bacillus subtilis* (SEQ ID NO:1 in WO2009149271).
(i) variants exhibiting at least 90% identity with the wild-type amylase from *Bacillus* sp. KSM-K38 with accession number AB051102.
(j) variants exhibiting at least 80% identity with the mature amino acid sequence of AAI10 from *Bacillus* sp (SEQ ID NO:7 in WO2016180748)
(k) variants exhibiting at least 80% identity with the mature amino acid sequence of *Alicyclobacillus* sp. amylase (SEQ ID NO:8 in WO2016180748)

Preferably the amylase is an engineered enzyme, wherein one or more of the amino acids prone to bleach oxidation have been substituted by an amino acid less prone to oxidation. In particular it is preferred that methionine residues are substituted with any other amino acid. In particular it is preferred that the methionine most prone to oxidation is substituted. Preferably the methionine in a position equivalent to 202 in SEQ ID NO:11 is substituted. Preferably, the methionine at this position is substituted with threonine or leucine, preferably leucine.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL®, ATLANTIC®, INTENSA® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, PREFERENZ S® series (including PREFERENZ S1000® and PREFERENZ S2000® and PURASTAR OXAM® (DuPont., Palo Alto, Calif.) and KAM® (Kao, 14-10 Nihonbashi Kayabacho, 1-chome, Chuo-ku Tokyo 103-8210, Japan). In one aspect, suitable amylases include ATLANTIC®, STAINZYME®, POWERASE®, INTENSA® and STAINZYME PLUS® and mixtures thereof.

Preferably, the product of the invention comprises at least 0.01 mg, preferably from about 0.05 to about 10, more preferably from about 0.1 to about 6, especially from about 0.2 to about 5 mg of active amylase/g of composition.

Preferably, the protease and/or amylase of the composition of the invention are in the form of granulates, the granulates comprise more than 29% of sodium sulfate by weight of the granulate and/or the sodium sulfate and the active enzyme (protease and/or amylase) are in a weight ratio of between 3:1 and 100:1 or preferably between 4:1 and 30:1 or more preferably between 5:1 and 20:1.

Crystal Growth Inhibitor

Crystal growth inhibitors are materials that can bind to calcium carbonate crystals and prevent further growth of species such as aragonite and calcite.

Examples of effective crystal growth inhibitors include phosphonates, polyphosphonates, inulin derivatives, polyitaconic acid homopolymers and cyclic polycarboxylates.

Suitable crystal growth inhibitors may be selected from the group comprising HEDP (1-hydroxyethylidene 1,1-diphosphonic acid), carboxymethylinulin (CMI), tricarballylic acid and cyclic carboxylates. For the purposes of this invention the term carboxylate covers both the anionic form and the protonated carboxylic acid form.

Cyclic carboxylates contain at least two, preferably three or preferably at least four carboxylate groups and the cyclic structure is based on either a mono- or bi-cyclic alkane or a heterocycle. Suitable cyclic structures include cyclopropane, cyclobutane, cyclohexane or cyclopentane or cycloheptane, bicyclo-heptane or bicyclo-octane and/or tetrhaydrofuran. One preferred crystal growth inhibitor is cyclopentane tetracarboxylate.

Cyclic carboxylates having at least 75%, preferably 100% of the carboxylate groups on the same side, or in the "cis" position of the 3D-structure of the cycle are preferred for use herein. It is preferred that the two carboxylate groups, which are on the same side of the cycle are in directly neighbouring or "ortho" positions.

Preferred crystal growth inhibitors include HEDP, tricarballylic acid, tetrahydrofurantetracarboxylic acid (THFTCA) and cyclopentanetetracarboxylic acid (CPTCA). The THFTCA is preferably in the 2c,3t,4t,5c-configuration, and the CPTCA in the cis,cis,cis,cis-configuration. Especially preferred crystal growth inhibitor for use herein is HEDP.

Also preferred for use herein are partially decarboxylated polyitaconic acid homopolymers, preferably having a level of decarboxylation is in the range of 50 mole % to 90 mole %. Especially preferred polymer for use herein is Itaconix TSI® provided by Itaconix.

The crystal growth inhibitors are present preferably in a quantity from about 0.01 to about 10%, particularly from about 0.02 to about 5% and in particular, from 0.05 to 3% by weight of the composition.

Metal Care Agents

Metal care agents may prevent or reduce the tarnishing, corrosion or oxidation of metals, including aluminium, stainless steel and non-ferrous metals, such as silver and copper. Preferably the composition of the invention comprises from 0.1 to 5%, more preferably from 0.2 to 4% and especially from 0.3 to 3% by weight of the product of a metal care agent, preferably the metal care agent is benzo triazole (BTA).

Glass Care Agents

Glass care agents protect the appearance of glass items during the dishwashing process. Preferably the composition of the invention comprises from 0.1 to 5%, more preferably from 0.2 to 4% and specially from 0.3 to 3% by weight of the composition of a metal care agent, preferably the glass care agent is a zinc containing material, specially hydrozincite. Other suitable glass care agents are polyethyleneimine (PEI). A particularly preferred PEI is Lupasol® FG, supplied by BASF.

The automatic dishwashing composition of the invention preferably has a pH as measured in 1% weight/volume aqueous solution in distilled water at 20° C. of from about 9 to about 12, more preferably from about 10 to less than about 11.5 and especially from about 10.5 to about 11.5. The automatic dishwashing composition of the invention preferably has a reserve alkalinity of from about 10 to about 20, more preferably from about 12 to about 18 at a pH of 9.5 as measured in NaOH with 100 grams of product at 20° C.

A preferred automatic dishwashing composition of the invention comprises:
  i) from 10 to 20% by weight of the composition of sodium percarbonate;
  ii) from 10% to 50% by weight of the composition of an organic complexing agent system, preferably the complexing agent system comprises MGDA;
  iii) TAED;
  iv) amylases;
  v) optionally but preferably from 5 to 50% by weight of the composition of an inorganic builder, preferably sodium carbonate;
  vi) optionally but preferably from 2 to 10% by weight of the composition of a non-ionic surfactant;
  vii) other optional ingredients include: a crystal growth inhibitor, preferably HEDP, and glass care agents.

A preferred automatic dishwashing composition of the invention comprises:
  i) from 10 to 20% by weight of the composition of bleach, preferably sodium percarbonate;
  ii) from 10% to 50% by weight of the composition of an organic complexing agent system;
  iii) a manganese bleach catalyst and optionally TAED;
  iv) amylases;
  v) optionally but preferably from 5 to 50% by weight of the composition of an inorganic builder, preferably sodium carbonate;
  vi) optionally but preferably from 2 to 10% by weight of the composition of a non-ionic surfactant;
  vii) optionally but preferably a glass care agent.

EXAMPLE 1

The compositions displayed in Table 1 are made. 3 g of each composition are dissolved in a litre of deionized water to produce a cleaning solution having a pH of 11. The protease of the invention is added to the cleaning solution at a level between 0.25-0.75 ppm.

TABLE 1

Automatic Dishwashing Compositions

| Ingredients (active weight %) | ADW Formula A | ADW Formula B | ADW Formula C |
|---|---|---|---|
| Solid ingredients | | | |
| Sodium carbonate | 41.7 | 41.7 | 41.7 |
| Sodium sulphate | 0.00 | 1.68 | 2.03 |
| MGDA | 21.0 | 0.00 | 10.1 |
| Sodium citrate | 0.00 | 19.2 | 10.1 |
| TAED | 1.68 | 1.68 | 1.68 |
| Sodium percarbonate | 12.6 | 12.6 | 12.6 |
| Sulfonated polymer | 2.5 | 2.5 | 2.5 |
| Bleach catalyst | 1.2 | 1.2 | 1.2 |
| Amylase | 0.11 | 0.11 | 0.11 |
| Liquid ingredients | | | |
| Lutensol TO7 | 19.3 | 19.3 | 19.3 |

Table 1: Automatic Dish Washing (ADW) Compositions
Amylase      Stainzyme ® Plus supplied by Novozymes
TAED         Tetraacetylethylenediamine
MGDA         Three-sodium methyl glycine diacetate supplied by BASF
Bleach catalyst   MnTACN (Manganese 1,4,7-Triazacyclononane)
Sulfonated polymer  Acusol 588 supplied by Dow Chemicals
Lutensol TO7    Nonionic surfactant supplied by BASF The compositions provide good c e bru ee re val.

EXAMPLE 2

Cleaning Performance in Detergent

Egg Yolk Stain

The automatic dishwashing (ADW) cleaning performance of the protease variants described herein was tested relative to the reference protease (having amino acid sequence SEQ ID:NO 1) using egg yolk (PAS-38, Center for Testmaterials BV, Vlaardingen, Netherlands) microswatches and the GSM-B detergent (see Table 1, below), pH 10.5 in microtiter plates (MTPs). Pre-punched PAS-38 (to fit in MTPs) rinsed and unrinsed swatches were used in this assay. Rinsed swatches were prepared by adding 180 μL 10 mM CAPS buffer pH 11 to MTPs containing the PAS-38 microswatches and shaking for 30 mM at 60° C. and 1100 rpm. After incubation, the buffer was removed, the swatches rinsed with deionized water to remove any residual buffer, and the MTPs air dried prior to use in the assay. All microswatch plates were filled prior to enzyme addition with 3 g/l GSM-B detergent adjusted to 374 ppm water hardness.

Alternatively, cleaning performance of variants on egg yolk stain was tested by using DM21 melamine tiles prepared by CFT (Vlaardingen, the Netherlands) as set forth herein. Egg yolk on melamine tiles were prepared by CFT using 2.5 g of material per tile.

The melamine tiles were used as a lid and tightly pressed onto a microtiter plate (MTP). DM21 tiles were prerinsed using 300 μL 10 mM CAPS pH 11 with 0.005% Tween-80 at 40° C. while shaking 250 rpm for 40 min. Tiles were rinsed with tap water and dried overnight. For cleaning, 3 g/L of GSMB (See Table 1) adjusted to 374ppm water hardness and each enzyme sample were added to the MTP prior to attaching the melamine tile lid to the MTP. The volume capacity of the MTP, and therefore the volume of solution added thereto, may vary, wherein a minimal volume of solution that enables contact between solution and stain surface should be added to the MTP. In this example, a volume of 300 μL of detergent containing enzyme was added to each well of an aluminum 96-well MTP. The MTPs were incubated in an Infors thermal shaker for 45 min at 40° C. at 250 rpm. After incubation, the tiles were removed from the MTP and air-dried.

Stain removal was quantified by photographing the plates and measuring the RGB values from each stain area using custom software. Percent Soil removal (% SRI) values of the washed tiles were calculated by using the RGB values in the following formula:

$$\% \text{ SRI} = (\Delta E / \Delta E_{initial}) * 100$$

$$\text{Where } \Delta E = \text{SQR}((R_{after} - R_{before})^2 + (G_{after} - G_{before})^2 + (B_{after} - B_{before})^2)$$

$$\text{Where } \Delta E_{initial} = \text{SQR}((R_{white} - R_{before})^2 + (G_{white} - G_{before})^2 + (B_{white} - B_{before})^2)$$

Cleaning performance was obtained by subtracting the value of a blank control (no enzyme) from each sample value (hereinafter "blank subtracted cleaning"). For each condition and variant, a performance index (PI) was calculated by dividing the blank subtracted cleaning by that of the reference protease (having the amino acid sequence SEQ ID NO:1) at the same concentration. The value for the reference protease PI was determined from a standard curve of the reference protease which was included in the test and which was fitted to a Langmuir fit.

Crème Brûlée stain

Crème Brûlée stain: The cleaning performance of the variants on crème brûlée stain was tested by using custom ordered melamine dishwasher monitors (tiles) prepared by CFT in Vlaardingen, the Netherlands as set forth herein, and labelled DM10c. The DM10c tiles used in this study are prepared using 2.7 g of the same material used to prepare the commercially available DM10 monitors (creme brulee Debic.com product) but baked at 140° C. for 2 hours, instead of 150° C.

TABLE 1

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

TABLE 2

MGDA pH 10.5 ADW Detergent Ingredients

| Component | Weight % |
|---|---|
| MGDA | 64.6 |
| Plurafac SLF 18-45D | 4.4 |
| Bismuthcitrate | 0.4 |
| Phosphonates (Bayhibit S) | 0.4 |
| Acusol 420/Acosul 587 | 1.6 |
| PEG6000 | 2.4 |
| PEG1500 | 5.9 |
| Sodium percarbonate | 16.1 |
| TAED | 4.1 |

AAPF Activity Assay

The protease activity of the reference protease and variants thereof was tested by measuring hydrolysis of N-suc- AAPF-pNA. The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM CaCl$_2$ and 0.005% TWEEN®-80 (Tris/Ca buffer); and 160 mM suc-AAPF-pNA in DMSO (suc-AAPF-pNA stock solution) (Sigma: S-7388). A substrate working solution was prepared by adding 1 mL suc-AAPF-pNA stock solution to 100 mL Tris/Ca buffer and mixed well. An enzyme sample was added to a MTP (Greiner 781101) containing 1 mg/suc-AAPF-pNA working solution and assayed for activity at 405 nm over 3 min with a SpectraMax plate reader in kinetic mode at room temperature (RT). The absorbance of a blank containing no protease was subtracted from each sample reading. The protease activity was expressed as mOD·min$^{-1}$.

Stability Assay

The stability of the variants described herein was measured by diluting the variants in stress buffer and measuring the proteolytic activity of the variants before and after a heat incubation step using the AAPF assay described above. The temperature and duration of the heat incubation step were chosen such that the reference protease showed ~50% residual activity. Stability was measured in Tris-EDTA (50 mM Tris pH 9; 5 mM EDTA; 0.005% Tween 80) buffered condition. Stability PIs were obtained by dividing the residual activity of the variant by that of the reference protease.

EXAMPLE 3

Performance of the Variants

The cleaning benefits of the reference protease and variants thereof made in accordance with Example 2 were evaluated in the following assays described in Example 2: PAS-38 or DM21 cleaning in GSM-B detergent, Crème Brulee (DM10c) cleaning in either GSM-B (Table 1) or MGDA (Table 2) detergents, and stability in Tris/EDTA. The results for these evaluations of the reference protease and variants thereof are reported as Performance Index (PI) values calculated versus the reference protease as described in Example 2 and are shown on Table 3. ND means the value was not determined or values were outside the confidence interval for the assays.

TABLE 3

Stability, ADW EGG Performance, Crème Brulee Cleaning Performance of Variants.

| SEQ ID NO: 1 with the following amino acid substitutions | Stability in EDTA with respect to reference protease (SEQ ID NO: 1) | ADW EGG performance with respect to reference protease (SEQ ID NO: 1) | | Crème Brulee cleaning performance with respect to reference protease (SEQ ID NO: 1) | |
|---|---|---|---|---|---|
| | | ADW Rinsed EGG Stain | ADW Unrinsed EGG Stain | GSM-B Detergent | MGDA Detergent |
| Q001C | 1.0 | <0.9 | 0.9 | 1.2 | 1.2 |
| Q001D | 1.0 | <0.9 | 0.9 | 1.5 | 1.1 |
| Q001E | 1.0 | <0.9 | 1.0 | 1.3 | 1.1 |
| Q001M | 1.0 | 1.0 | 1.0 | 1.2 | 1.1 |
| Q001N | 1.0 | 1.0 | 1.0 | 1.3 | 1.1 |
| I021L | 1.0 | 1.0 | 1.0 | 1.1 | 1.4 |
| T037A | 1.0 | <0.9 | <0.9 | 1.4 | <0.9 |
| T054A | 1.1 | <0.9 | <0.9 | 0.9 | 0.9 |
| L073V | 1.0 | 1.0 | 1.0 | 1.3 | 1.7 |
| S076D | 1.0 | 0.9 | 0.9 | 1.5 | 1.6 |
| S076H | 1.0 | 1.0 | 1.0 | 1.3 | 1.0 |
| S076N | 1.0 | 1.0 | 1.0 | 1.3 | <0.9 |
| S076T | 1.0 | 1.0 | 1.0 | 1.1 | 1.0 |
| A083G | 1.1 | 0.9 | 0.9 | 0.9 | 0.9 |
| P084D | 1.0 | 1.0 | 1.0 | 1.8 | 1.8 |
| P084E | 1.0 | 1.0 | 1.0 | 1.7 | 1.6 |
| P084F | 1.1 | 1.0 | 1.1 | 0.9 | 1.0 |
| S085I | 1.0 | 1.1 | 1.0 | 1.0 | 1.0 |
| S085M | 1.0 | 1.0 | 1.0 | 1.5 | 1.4 |
| A086I | 1.0 | 1.2 | 1.1 | 1.2 | 0.9 |
| A086S | 1.0 | 1.1 | 1.1 | <0.9 | <0.9 |
| A086T | 1.0 | 1.1 | 1.1 | 1.1 | <0.9 |
| A086V | 1.0 | 1.1 | 1.0 | 0.9 | <0.9 |
| D087T | 1.3 | 1.0 | 0.9 | 0.9 | <0.9 |
| L088M | 1.0 | <0.9 | 0.9 | 1.0 | 1.1 |
| L088V | 1.0 | 1.1 | 1.0 | 1.2 | 1.0 |
| Y089F | 1.0 | 1.1 | 1.1 | 0.9 | 1.1 |
| Y089W | 1.1 | 1.0 | 0.9 | 1.0 | 0.9 |
| V091I | 1.0 | 1.0 | 1.1 | 1.0 | <0.9 |
| G095A | 1.1 | 0.9 | 0.9 | 1.0 | 1.3 |
| G095N | 1.1 | 1.0 | 1.0 | <0.9 | 1.0 |
| G095S | 1.1 | <0.9 | <0.9 | <0.9 | <0.9 |
| A096M | 1.0 | 0.9 | 1.0 | 0.9 | 1.7 |
| A096Q | 1.0 | 1.0 | 1.0 | 1.0 | 1.3 |
| N097E | 1.3 | <0.9 | 1.0 | 1.2 | 1.9 |
| G098M | 1.1 | <0.9 | <0.9 | <0.9 | <0.9 |
| R099A | 1.4 | <0.9 | <0.9 | 1.1 | 1.9 |
| R099F | 1.5 | <0.9 | <0.9 | 0.9 | 1.1 |
| R099H | 1.5 | <0.9 | <0.9 | 1.4 | 1.7 |
| R099I | 1.3 | <0.9 | <0.9 | 0.9 | 1.1 |
| R099K | 1.1 | <0.9 | 1.1 | <0.9 | 1.0 |
| R099L | 1.3 | <0.9 | 0.9 | <0.9 | 1.2 |

TABLE 3-continued

Stability, ADW EGG Performance, Crème Brulee Cleaning Performance of Variants.

| SEQ ID NO: 1 with the following amino acid substitutions | Stability in EDTA with respect to reference protease (SEQ ID NO: 1) | ADW EGG performance with respect to reference protease (SEQ ID NO: 1) | | Crème Brulee cleaning performance with respect to reference protease (SEQ ID NO: 1) | |
|---|---|---|---|---|---|
| | | ADW Rinsed EGG Stain | ADW Unrinsed EGG Stain | GSM-B Detergent | MGDA Detergent |
| R099Q | 1.3 | <0.9 | <0.9 | 1.5 | 2.0 |
| R099T | 1.3 | <0.9 | <0.9 | 1.6 | 2.0 |
| R099W | 1.4 | <0.9 | <0.9 | <0.9 | <0.9 |
| R099Y | 1.3 | <0.9 | <0.9 | 1.1 | 1.1 |
| V102L | 1.1 | 1.0 | 1.0 | <0.9 | <0.9 |
| G104E | 1.0 | <0.9 | <0.9 | 2.3 | 2.0 |
| I105L | 1.2 | <0.9 | <0.9 | <0.9 | <0.9 |
| A106I | 1.2 | 0.9 | 0.9 | <0.9 | 0.9 |
| A106V | 1.3 | 1.0 | 1.0 | <0.9 | 0.9 |
| Q107E | 1.4 | <0.9 | 0.9 | 1.6 | 1.5 |
| G108A | 1.1 | 1.1 | 1.0 | <0.9 | <0.9 |
| L109I | 1.0 | 1.1 | 1.1 | <0.9 | <0.9 |
| A112C | 1.0 | 1.0 | 1.1 | 1.1 | 0.9 |
| Q114A | 1.0 | 1.1 | 1.2 | 0.9 | <0.9 |
| Q114M | 1.1 | 1.1 | 1.2 | 1.0 | <0.9 |
| Q114N | 1.1 | 1.1 | 1.1 | 0.9 | 0.9 |
| N115A | 1.1 | 1.1 | 1.0 | 1.2 | 1.1 |
| N115E | 1.3 | 1.0 | 1.0 | 1.2 | 1.7 |
| N115H | 1.0 | 1.0 | 1.0 | 1.1 | 1.0 |
| N115Q | 1.0 | 1.1 | 1.0 | 1.0 | 1.2 |
| N116A | 1.0 | 1.0 | 1.0 | 1.0 | 1.1 |
| N116E | 1.2 | 0.9 | 0.9 | 1.1 | 1.7 |
| N116G | 1.0 | 1.0 | 1.0 | 1.2 | 1.0 |
| N116H | 1.0 | 1.0 | 1.0 | 1.1 | 1.0 |
| N116Q | 1.0 | 1.1 | 1.0 | <0.9 | 1.2 |
| M117I | 0.8 | 1.1* | ND | 0.7 | ND |
| H118A | 1.1 | 1.0 | 1.0 | 0.9 | <0.9 |
| H118D | 1.1 | 1.1 | 1.1 | <0.9 | 1.1 |
| H118N | 1.0 | 1.1 | 1.1 | 0.9 | <0.9 |
| M122C | 1.4 | 0.9 | 1.1 | <0.9 | <0.9 |
| L124E | 1.1 | <0.9 | ND | <0.9 | <0.9 |
| L124Q | 1.2 | <0.9 | <0.9 | <0.9 | <0.9 |
| A126I | 1.4 | 1.0 | 1.2 | <0.9 | <0.9 |
| A126Q | 1.2 | 1.1 | 1.2 | <0.9 | <0.9 |
| A126T | 1.3 | 1.0 | 1.1 | <0.9 | <0.9 |
| A126V | 1.4 | 0.9 | 1.2 | <0.9 | <0.9 |
| G128H | 1.3 | 1.0 | 1.0 | <0.9 | <0.9 |
| G128I | 1.2 | 1.0 | 1.0 | <0.9 | <0.9 |
| G128L | 1.2 | 1.0 | 0.9 | <0.9 | <0.9 |
| G128M | 1.2 | 1.0 | 0.9 | <0.9 | <0.9 |
| G128N | 1.2 | 1.0 | 1.0 | <0.9 | <0.9 |
| G128Q | 1.2 | 0.9 | 0.9 | <0.9 | <0.9 |
| G128S | 1.4 | 1.1 | 1.0 | <0.9 | <0.9 |
| G128T | 1.3 | 1.1 | 1.0 | <0.9 | <0.9 |
| G128V | 1.3 | 1.0 | 1.1 | <0.9 | <0.9 |
| G128Y | 1.2 | <0.9 | 0.9 | <0.9 | <0.9 |
| P129D | 1.4 | <0.9 | 0.9 | 1.2 | 1.4 |
| P129H | 1.1 | 0.9 | 1.0 | <0.9 | <0.9 |
| S130N | 1.0 | 1.2 | 1.0 | <0.9 | <0.9 |
| S131D | 1.6 | <0.9 | 1.0 | 1.5 | 1.4 |
| S131E | 1.5 | <0.9 | 1.0 | 1.3 | 1.5 |
| S131N | 1.1 | 1.1 | 1.1 | 1.1 | <0.9 |
| S131P | 1.2 | 1.0 | 1.1 | 0.9 | <0.9 |
| S131Q | 1.2 | 1.0 | 0.9 | 0.9 | 0.9 |
| S131T | 1.1 | 0.9 | 0.9 | 1.0 | 1.0 |
| R135A | 1.5 | <0.9 | 0.9 | 1.2 | 1.2 |
| R135D | 1.4 | 0.9 | 1.0 | <0.9 | 0.9 |
| R135H | 1.5 | <0.9 | 1.0 | 1.5 | 1.5 |
| R135K | 1.1 | 0.9 | 1.0 | 1.2 | 1.2 |
| R135L | 1.5 | <0.9 | 0.9 | 1.9 | 2.0 |
| R135M | 1.4 | <0.9 | 0.9 | 1.3 | 1.2 |
| R135N | 1.5 | <0.9 | 0.9 | 1.1 | 1.2 |
| R135Q | 1.5 | <0.9 | 0.9 | 1.4 | 1.4 |
| R135T | 2.0 | <0.9 | 1.0 | 1.6 | 1.6 |
| R135V | 1.4 | 0.9 | 1.1 | 1.7 | 1.8 |
| R135W | 1.5 | <0.9 | 0.9 | 1.7 | 1.6 |
| R135Y | 1.5 | <0.9 | 1.0 | 1.6 | 1.8 |
| N138D | 1.4 | 0.9 | 0.9 | 1.1 | 1.3 |
| N138E | 1.2 | <0.9 | <0.9 | 0.9 | 1.0 |
| Y139E | 1.5 | 1.1 | 1.1 | 1.2 | 1.2 |

TABLE 3-continued

Stability, ADW EGG Performance, Crème Brulee Cleaning Performance of Variants.

| SEQ ID NO: 1 with the following amino acid substitutions | Stability in EDTA with respect to reference protease (SEQ ID NO: 1) | ADW EGG performance with respect to reference protease (SEQ ID NO: 1) | | Crème Brulee cleaning performance with respect to reference protease (SEQ ID NO: 1) | |
|---|---|---|---|---|---|
| | | ADW Rinsed EGG Stain | ADW Unrinsed EGG Stain | GSM-B Detergent | MGDA Detergent |
| Y139L | 1.0 | 1.2 | 1.2 | 1.7 | 1.4 |
| T141A | 1.1 | 1.1 | 1.1 | 0.9 | 1.1 |
| T141E | 1.2 | 1.0 | 1.1 | 1.0 | 1.4 |
| T141F | 1.1 | 0.9 | 1.0 | <0.9 | 1.0 |
| T141H | 1.0 | 1.0 | 0.9 | 1.3 | 1.1 |
| T141Y | 1.0 | 1.1 | 1.1 | 1.8 | 1.5 |
| S142A | 1.0 | 1.1 | 1.1 | <0.9 | <0.9 |
| S142D | 1.5 | 0.9 | 1.0 | 1.2 | 1.4 |
| S142E | 1.5 | 0.9 | 0.9 | 1.3 | 1.4 |
| R143A | 1.3 | 1.0 | 1.0 | 1.7 | 1.3 |
| R143E | 1.4 | <0.9 | 0.9 | 1.3 | 1.2 |
| R143H | 1.4 | 0.9 | 1.0 | 1.3 | 1.6 |
| R143K | 1.1 | 0.9 | 0.9 | 1.2 | 1.2 |
| R143M | 1.3 | <0.9 | 0.9 | 1.3 | 1.2 |
| R143Q | 1.3 | 0.9 | 1.0 | 1.4 | 1.3 |
| R143S | 1.2 | <0.9 | <0.9 | 1.4 | 1.8 |
| R143V | 1.3 | 0.9 | 1.0 | 1.3 | 1.3 |
| N154D | 1.3 | <0.9 | 1.1 | 1.6 | 1.5 |
| S156E | 1.2 | <0.9 | 1.0 | 2.0 | 1.9 |
| G157C | 1.3 | <0.9 | 0.9 | 0.9 | 1.2 |
| G157D | 1.4 | <0.9 | <0.9 | 1.8 | 1.8 |
| G157E | 1.4 | <0.9 | 0.9 | 1.5 | 1.7 |
| M211D | 1.2 | 2.1* | ND | <0.9 | ND |
| M211E | 0.7 | 1.3* | ND | 2.4 | ND |
| M211N | 0.5 | 1.2* | ND | 1.3 | ND |
| M211Q | 0.7 | 1.2* | ND | 1.4 | ND |
| M216Q | 1.6 | 0.9* | ND | 0.5 | ND |

*denotes PI values obtained from assays performed using DM21 tiles

The following variants showed improved performance index (PI value of >1.1) compared to the reference protease on one of the following assays: PAS-38 (rinsed or unrinsed) or crème brûlée (GSMB or MGDA detergent) ADW cleaning, or stability in Tris-EDTA buffer: Q001C/D/E/M/N, I021L, T037A, T054A, L073V, S076D/H/N/T, A083G, P084D/E/F, S085I/M, A0861/S/T/V, D087T, L088M/V, Y089F/W, V0911, G095A/N/S, A096M/Q, N097E, G098M, R099A/F/H/I/K/L/Q/T/W/Y, V102L, G104E, I105L, A106I/V, Q107E, G108A, L109I, A112C, Q114A/M/N, N115A/E/H/Q, N116A/E/G/H/Q, M117I, H118A/D/N, M122C, L124E/Q, A126I/Q/T/V, G128H/I/L/M/N/Q/S/T/V/Y, P129D/H, S130N, S131D/E/N/P/Q/T, R135A/D/H/K/L/M/N/Q/T/V/W/Y, N138D/E, Y139E/L, T141A/E/F/H/Y, S142A/D/E, R143A/E/H/K/M/Q/S/V, N154D, S156E, G157C/D/E, M211D/E/N/Q, M216Q The following variants showed improved ADW cleaning performance index (PI value of ≥1.1) compared to the reference protease in at least one of the PAS-38 assays: P084F, S0851, A0861/S/T/V, Y089F, V0911, G108A, L109I, A112C, Q114A/M/N, N115A, N116Q, M117I, H118N, M122C, A126I/Q/T/V, G128T/V, S130N, S131N, Y139E/L, T141A/E/Y, S142A, N154D, M211D/E/N/Q The following variants showed improved ADW cleaning performance index (PI value of ≥1.1) compared to the reference protease in at least one of the crème Brûlée assays: Q001C/D/E/N, I021L, T037A, L073V, S076D/H/N, P084D/E, S085M, G095A, A096M/Q, N097E, R099A/H/Q/T, G104E, Q107E, N115E, N116E/G, P129D, S131D/E, R135H/K/L/M/Q/T/V/W/Y, N138D, Y139E/L, T141E/H/Y, S142D/E, R143A/E/H/K/M/Q/S/V, N154D, S156E, G157D/E, M211E/N/Q The following variants showed improved stability (PI value of ≥1.1) compared to the reference protease in Tris-EDTA buffer: T054A, A083G, P084F, A086V, D087T, L088M, Y089W, G095A/N/S, N097E, G098M, R099A/F/H/I/K/L/Q/T/W/Y, V102L, I105L, A106I/V, Q107E, G108A, Q114M/N, N115A/E, N116E, H118A/D, M122C, L124E/Q, A126I/Q/T/V, G128H/I/L/M/N/Q/S/T/V/Y, P129D/H, S131D/E/N/P/Q/T, R135A/D/H/K/L/M/N/Q/T/V/W/Y, N138D/E, Y139E, T141A/E/F, S142D/E, R143A/E/H/K/M/Q/S/V, N154D, S156E, G157C/D/E, M211D, M216Q The following variants showed improved performance index (PI value of >1.1) compared to the reference protease in at least one of the PAS-38 assays or in at least one of the creme brill& assays and improved stability in Tris-EDTA buffer: P084F, A086V, G095A, N097E, R099A/H/Q/T, Q107E, G108A, Q114M/N, N115A/E, N116E, M122C, A126I/Q/T/V, G128T/V, P129D, S131D/E/N, R135H/K/L/M/Q/T/V/W/Y, N138D, Y139E, T141A/E, S142D/E, R143A/E/H/K/M/Q/S/V, N154D, S156E, G157D/E, M211D The following variants showed improved performance index (PI value of ≥1.1) and a reduced net charge compared to the reference protease in at least one of the PAS-38 or crème brûlée assays : Q001C/D/E, S076D, P084D/E, N097E, R099A/H/Q/T, G104E, Q107E, N115E, N116E, P129D, S131D/E, R135H/K/L/M/Q/T/V/W/Y, N138D, Y139E, T141E/Y, S142D/E, R143A/E/H/K/M/Q/S/V, N154D, S156E, G157D/E, M211E The following variants showed improved stability (PI value of ≥1.1) and a reduced net charge compared to the reference protease in Tris-EDTA buffer: N097E, R099A/F/H/I/K/L/Q/T/W/Y, Q107E, N115E, N116E, H118D, M122C, L124E, G128Y, P129D, S131D/E, R135A/D/H/K/L/M/N/Q/T/V/W/Y, N138D/E, Y139E, T141E, S142D/E, R143A/E/H/K/M/Q/S/V, N154D, S156E, G157C/D/E, M211D The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An automatic dishwashing cleaning composition comprising a protease wherein the protease is a variant having at least about 90% identity with the amino acid sequence of SEQ ID NO:1 and the variant comprises one or more amino acid substitutions at one or more positions corresponding to SEQ ID NO: 1 positions selected from the group consisting of:
   (i) 54A, 73V, 76D/H/N/T, 83G, 84D/E/F, 86I/S/T/V, 88M/V, 89F/W, 91I, 95A/N/S, 96M/Q, 97E, 98M, 102L, 104E, 105L, 106I/V, 108A, 109I, 112C, 115A/E/H/Q, 118A/D/N, 122C, 124E/Q, 129D/H, 130N, 131D/E/N/P/Q, 138D/E, 139E/L, 141A/E/F/H/Y, 142A/D/E, 143E/H/K/M/S/V, 156E, and 157C/D/E;
   wherein the amino acid positions of the variant are numbered by correspondence with the amino acid sequence of SEQ ID NO: 1, wherein the composition further comprises:
   i) from about 10% to about 50% by weight of the composition of an organic complexing agent system;
   ii) a bleaching system comprising at least about 10% by weight of the composition of percarbonate;
   iii) a non-ionic surfactant;
   iv) a dispersant polymer; and
   v) an amylase.

2. A composition according to claim 1 wherein the variant comprises one or more amino acid substitutions at one or more positions corresponding to SEQ ID NO: 1 positions selected from the group consisting of:
   73V; 76D; 84D/E; 86I/V; 96M; 97E; 104E; 106I/V; 115A/E; 122C; 129D; 130N; 131D/E; 135A/D/H/L/M/N/Q/T/V/W/Y; 138D; 139E/L; 141E/Y; 142D/E; 143E/H/M/V; 156E; and 157C/D/E.

3. A composition according to claim 1 wherein the protease is a variant having at least about 95% identity with the amino acid sequence of SEQ ID NO:1.

4. A composition according to claim 1 wherein the composition is phosphate free.

5. A composition according to claim 1 comprising a bleach activator and/or a bleach catalyst.

6. A composition according to claim 1 comprising a bleach catalyst comprising a manganese catalyst.

7. A composition according to claim 1 wherein the complexing agent system comprises a complexing agent selected from the group consisting of citric acid, methyl glycine diacetic acid, glutamic-N,N-diacetic acid, iminodisuccinic acid, carboxy methyl inulin, their salts, and mixtures thereof.

8. A composition according to claim 1 wherein the complexing agent system comprises a salt of methyl glycine diacetic acid.

9. A composition according to claim 1 wherein the complexing agent system comprises citric acid and methyl glycine diacetic acid in a weight ratio of from about 0.5:1 to about 2:1.

10. A composition according to claim 1 wherein the amylase is an alpha amylase preferably having a mutation in position equivalent to 202 in SEQ ID No. 2.

11. A composition according to claim 1 wherein the dispersant polymer comprises a carboxylated/sulfonated polymer.

12. A method of washing soiled dishware in a dishwasher comprising the steps of:
   i) providing the soiled dishware; treating the dishware with a cleaning composition according to claim 1; and rinsing the dishware.

13. The composition according to claim 10, wherein the mutation is an amino acid substitution of methionine with threonine or leucine.

* * * * *